(12) United States Patent
Hyatt et al.

(10) Patent No.: US 8,965,534 B2
(45) Date of Patent: Feb. 24, 2015

(54) APPARATUS AND METHOD FOR ENERGY DISTRIBUTION IN A MEDICAL ELECTRODE

(71) Applicant: Covidien LP, Mansfield, MA (US)

(72) Inventors: Christopher J. Hyatt, South Hadley, MA (US); Scott R. Coggins, Littleton, MA (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 14/010,880

(22) Filed: Aug. 27, 2013

(65) Prior Publication Data

US 2014/0073896 A1    Mar. 13, 2014

Related U.S. Application Data

(60) Provisional application No. 61/700,334, filed on Sep. 13, 2012.

(51) Int. Cl.
*A61N 1/04*    (2006.01)
*A61B 5/04*    (2006.01)
*A61B 5/0408*  (2006.01)

(52) U.S. Cl.
CPC .............. *A61B 5/04* (2013.01); *A61B 5/04087* (2013.01); *A61N 1/048* (2013.01); *A61N 1/0492* (2013.01); *A61B 2562/125* (2013.01); *A61N 1/046* (2013.01)
USPC .......................................... 607/142; 607/152

(58) Field of Classification Search
USPC .................................................. 607/142, 152
See application file for complete search history.

(56) References Cited

U.S. PATENT DOCUMENTS

| | | | |
|---|---|---|---|
| 5,824,033 A | 10/1998 | Ferrari | |
| 6,600,957 B2 | 7/2003 | Gadsby | |
| 6,999,822 B2 * | 2/2006 | Koike | ........................... 607/142 |
| 7,169,644 B2 | 1/2007 | Ferrari | |
| 7,697,997 B2 * | 4/2010 | Hyatt et al. | ................... 607/142 |
| 7,742,828 B2 | 6/2010 | Gadsby et al. | |
| 2010/0152827 A1 * | 6/2010 | Wilfinger | ...................... 607/142 |

OTHER PUBLICATIONS

Korean Office Action; Received Sep. 11, 2014; For Korean Pat. App. No. 10-2013-0109689; 5 Pages.

\* cited by examiner

*Primary Examiner* — Catherine Voorhees
*Assistant Examiner* — Michael Carey
(74) *Attorney, Agent, or Firm* — Lisa E. Winsor, Esq.

(57) ABSTRACT

A medical electrode includes an electrode member having a top face and a bottom face, an electrical conductor having an unfanned, unsheathed end portion for conducting energy between the electrode member and a medical device, and a patient contacting layer secured to at least a portion of the bottom face of the electrode member. An energy blocking layer is disposed between the unfanned conductor end portion and the electrode member to prevent immediate transfer of energy to the electrode member. A current distributing structure is described to conduct and distribute energy to the electrode member.

23 Claims, 6 Drawing Sheets

APPARATUS AND METHOD FOR ENERGY DISTRIBUTION IN A MEDICAL ELECTRODE

RELATED APPLICATIONS

This application claims priority under 35 U.S.C. 119(e) to U.S. application Ser. No. 61/700,334 filed on Sep. 13, 2012 entitled APPARATUS AND METHOD FOR ENERGY DISTRIBUTION INA MEDICAL ELECTRODE, which is incorporated herein by reference in its entirety for all purposes.

FIELD OF THE INVENTION

This invention relates generally to medical electrodes and, more particularly, to a multifunction medical electrode with improved manufacturability and reduced cost.

BACKGROUND OF THE INVENTION

Conventional medical electrodes generally include a conductive electrode member and an electrical conductor that provides an electrical interface between the electrode and various types of medical equipment, such as monitoring equipment and stimulating equipment. Illustrative monitoring equipment includes electrocardiograph (ECG) monitors and illustrative stimulating equipment includes transcutaneous stimulation equipment and defibrillators.

Some known electrodes, referred to as multifunction electrodes, are designed to meet the requirements of different types of medical equipment so that the electrodes can be used for various medical procedures without requiring removal from the patient. For example, defibrillation electrodes deliver high energy levels, such as in the order of 360 Joules, over a relatively large area of the patient's skin, such as 50 $cm^2$ per electrode, in order to achieve sufficient current density distribution for restoring normal heartbeat rhythm. Challenges in designing defibrillation electrodes include avoiding irritation and burning of the patient's skin due to the high current density around the perimeter of defibrillation electrodes. Monitoring electrodes on the other hand are generally smaller, such as on the order of a few $cm^2$, and need to carry only very low level electrical signals in the order of milliamps. In order to permit X-ray examination without requiring removal of electrodes, X-ray transmissivity (referred to also as X-ray translucency and X-ray transparency) is a desirable characteristic for multifunction medical electrodes. Multifunction electrodes described in a U.S. Pat. No. 5,824,033 entitled "Multifunction Electrode" are optimized to meet these and other desirable characteristics of multifunction medical electrodes.

One of the difficulties in manufacturing medical electrodes has been attachment of the electrical conductor which is generally in the form of a multi-strand wire or fiber. In the electrodes described in the above-referenced U.S. Pat. No. 5,824,033 and others, generally, the individual conductor strands are spread, or fanned out and attached to a current distributing mat which, in turn, distributes current over a central area of the electrode member. However, fanning out the individual conductor strands is a manual process which is time consuming and costly.

SUMMARY OF THE INVENTION

In one aspect of the invention, a medical electrode includes an electrode member having a top face and a bottom face, an electrical conductor having an unfanned, unsheathed end portion for conducting energy between the electrode member and a medical device, an energy blocking layer disposed between the electrode member and the unfanned, unsheathed end portion of the electrical conductor, and a patient contacting layer secured to at least a portion of the bottom face of the electrode member. A current distributing structure is provided for conducting and distributing energy to an area of the electrode member. The energy blocking member may comprise a hydrophobic polymeric film and prevents the immediate transfer of charge from the conductor to the electrode member.

In one embodiment, the current distributing structure includes a first portion in the form of a current distributing layer disposed between the unfanned conductor end portion and a cover sheet secured to at least a portion of the top face of the electrode member and a second portion in the form of a current distributing mat disposed between the energy blocking layer and the electrode member. In another embodiment, the second portion of the current distributing structure is in the form of a current distributing mat disposed between the unfanned conductor end portion and the energy blocking layer. The current distributing structure may comprise one or more of a solid metallic foil, a mat comprising a metalized carbon fiber web, and an electrically conductive adhesive.

With this arrangement, charge from the unfanned, unsheathed conductor end portion is dispersed on the current distributing structure and subsequently transferred to the electrode member. For example, charge is dispersed outward on the current distributing layer and is then transferred from the current distributing layer directly to areas of the electrode member in some embodiments. In other embodiments, charge is transferred from the current distributing layer to areas of the electrode member through a current distributing mat. The current distributing layer serves the purpose of dispersing the electrical charge so as to effectively increase the contact area between the conductor and electrode member, as was conventionally achieved by fanning out the individual conductor strands. Elimination of the need to fan out the individual conductor strands permits automated, and thus less costly, manufacture of the electrode.

The electrode may further include a conductive coating in contact with at least a portion of the bottom face of the electrode member, such as may comprise a metal and metal chloride. A removable release carrier sheet covers the patient contacting layer and is adapted to be removed from the electrode for use on a patient. All or a portion of the electrode components may be transmissive to X-rays.

Also described is a method for fabricating a medical electrode including providing an electrode member with a top face and a bottom face, conductively coupling an unfanned, unsheathed end portion of an electrical conductor to the top face of the electrode member, the electrical conductor adapted to conduct energy between electrode member and a medical device, and securing a patient contacting layer to at least a portion of the bottom face of the electrode member. An energy blocking layer is provided between the unfanned, unsheathed end portion of the electrical conductor and the top face of the electrode member and a current distributing structure may be secured to at least a portion of the top face of the electrode member.

BRIEF DESCRIPTION OF THE DRAWINGS

The foregoing features of the invention, as well as the invention itself may be more fully understood from the following detailed description of the drawings, in which.

DETAILED DESCRIPTION OF THE INVENTION

Figure 1:
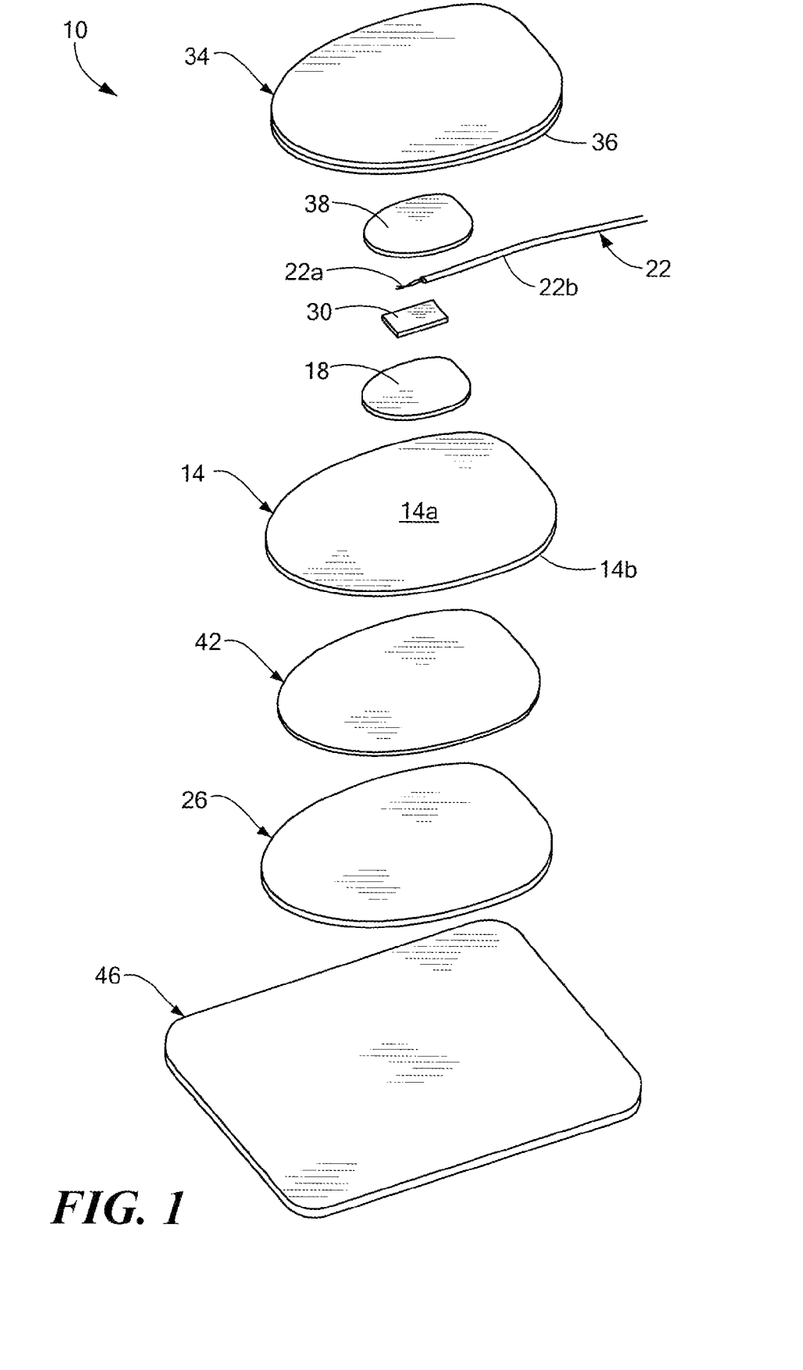
FIG. 1 is a perspective exploded view of a medical electrode according to a first embodiment.

Referring to the exploded view of FIG. 1, a medical electrode 10 includes a conductive electrode member 14 having a top face 14a and a bottom face 14b, an electrical conductor 22 having an unfanned, unsheathed end portion 22a for conducting energy between the electrode member and a medical device (FIG. 6), and a patient contacting layer 26 secured to at least a portion of the bottom face of the electrode member. By providing the electrode 10 with an electrical conductor having an unfanned end portion 22a, the manufacture of the electrode is suitable for automation, and therefore, simplified as compared to conventional medical electrodes in which the individual strands of the electrical conductor are manually fanned out.

An energy blocking layer 30 is disposed between the unfanned, unsheathed conductor end portion 22a and the top face 14a of the electrode member 14. The energy blocking layer 30 prevents the immediate transfer of energy from the conductor 22 to the electrode member 14.

In one embodiment, the energy blocking layer 30 comprises a hydrophobic polymeric film and may include, but is not limited to a nylon, vinyl, styrene, polyester, polyolefin, polyethylene, polyamide, polyimide, polypropylene, polystyrene, paper, products available from DuPont under the trademarks TYVEK® and TYPAR®, and products available from Fiber Filtration under the trademark REEMAY® and may have a thickness on the order of 0.005 inches. A hydrophobic polymeric film of this thickness is X-ray transparent as may be desirable in certain medical applications. Suitable sheet films are available from the Plastics and Adhesives division of Tyco International Ltd. The energy blocking layer 30 may be a closed cell polypropylene foam and may have a high dielectric value, such as on the order of greater than 500,000 ohms.

The energy blocking layer 30 may be a self-adhesive layer with adhesive on both its top and bottom surfaces and the adhesive on the energy blocking layer 30 may or may not be conductive. In one illustrative embodiment, the energy blocking layer 30 is on the order of 2 inches by 0.25 inches and is positioned longitudinally with respect to the unsheathed conductor end portion 22a.

Figure 3:
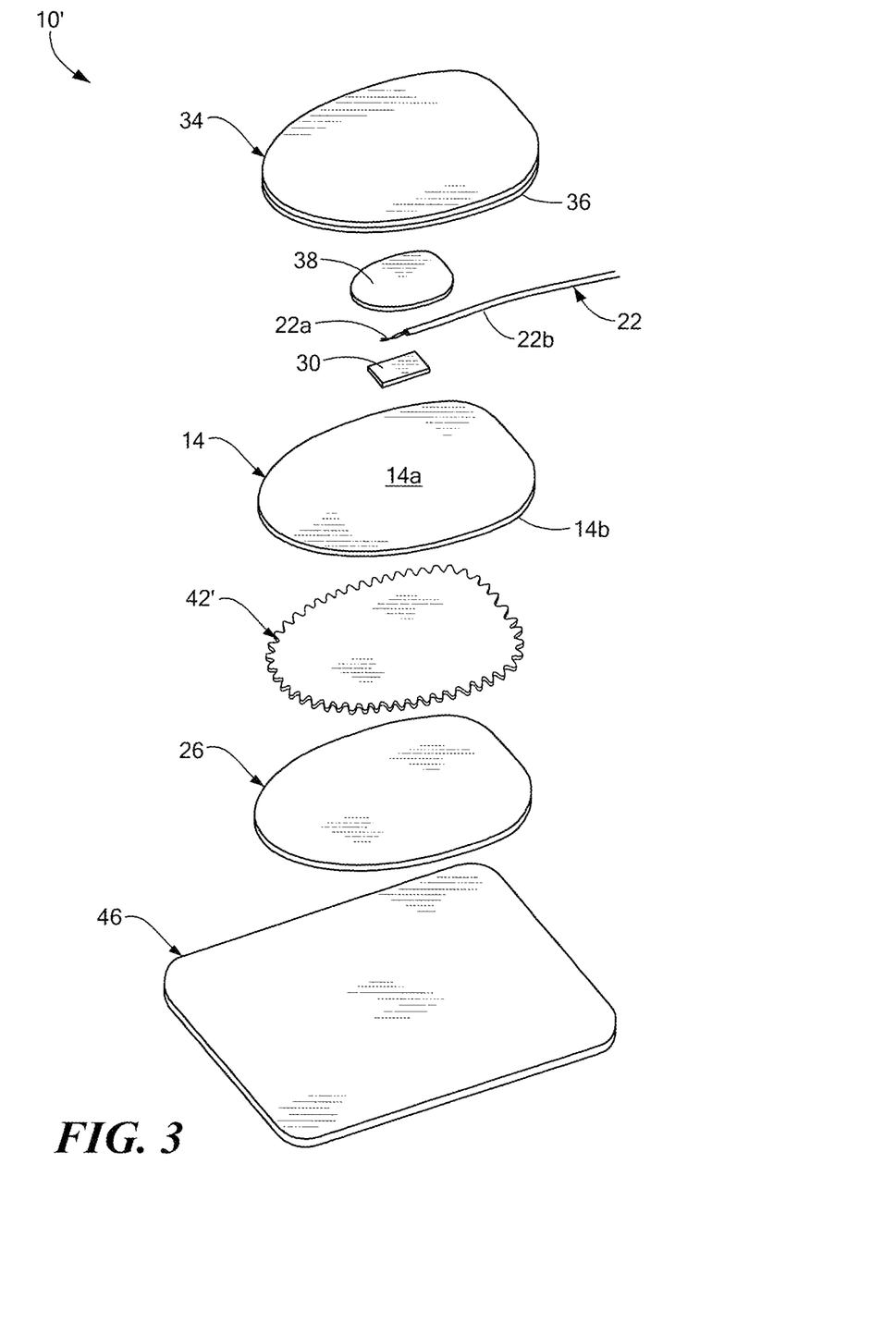
FIG. 3 is a perspective exploded view of a medical electrode according to an alternative embodiment.
Figure 4:
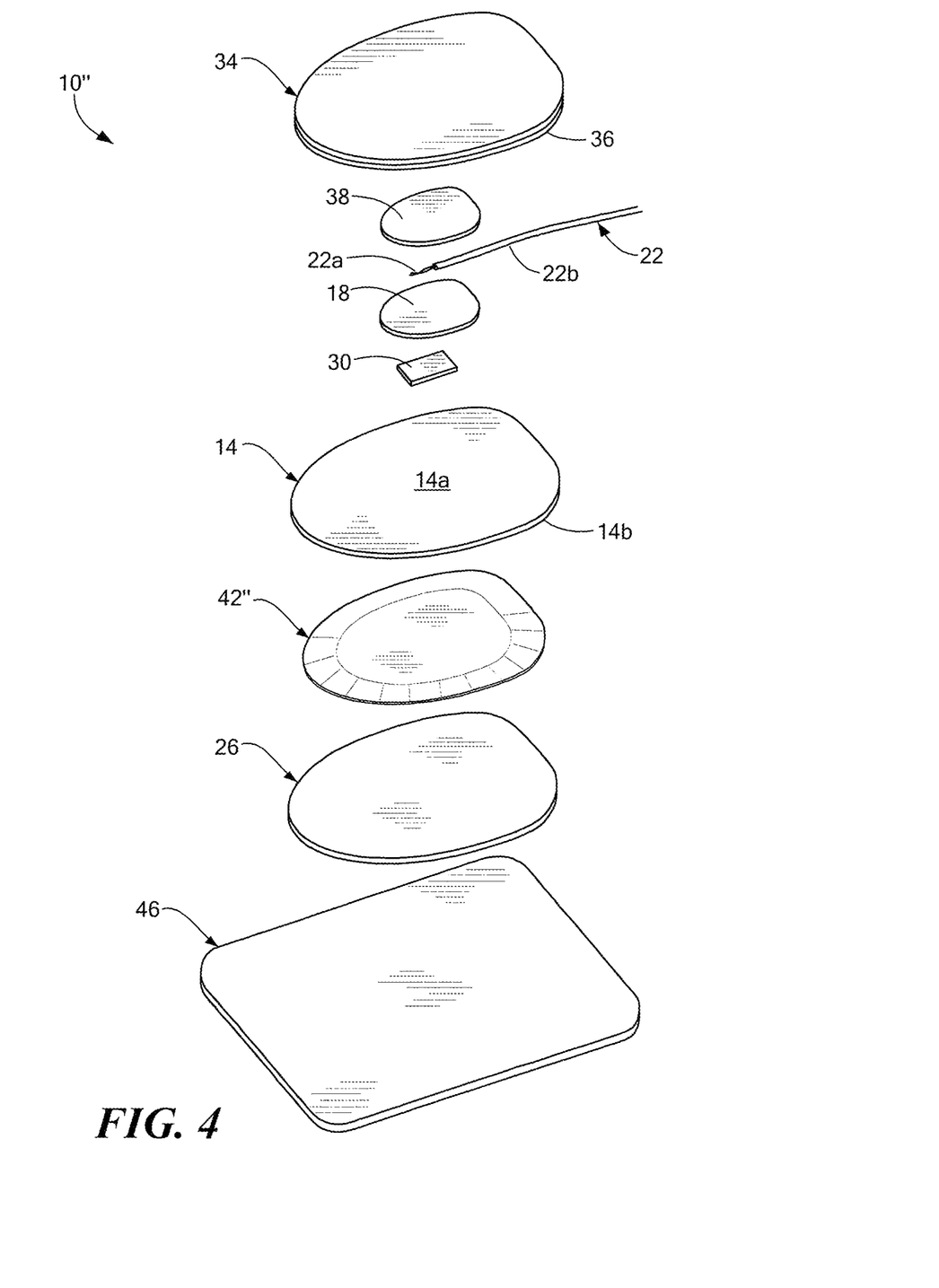
FIG. 4 is a perspective exploded view of a medical electrode according to another alternative embodiment.
Figure 5:
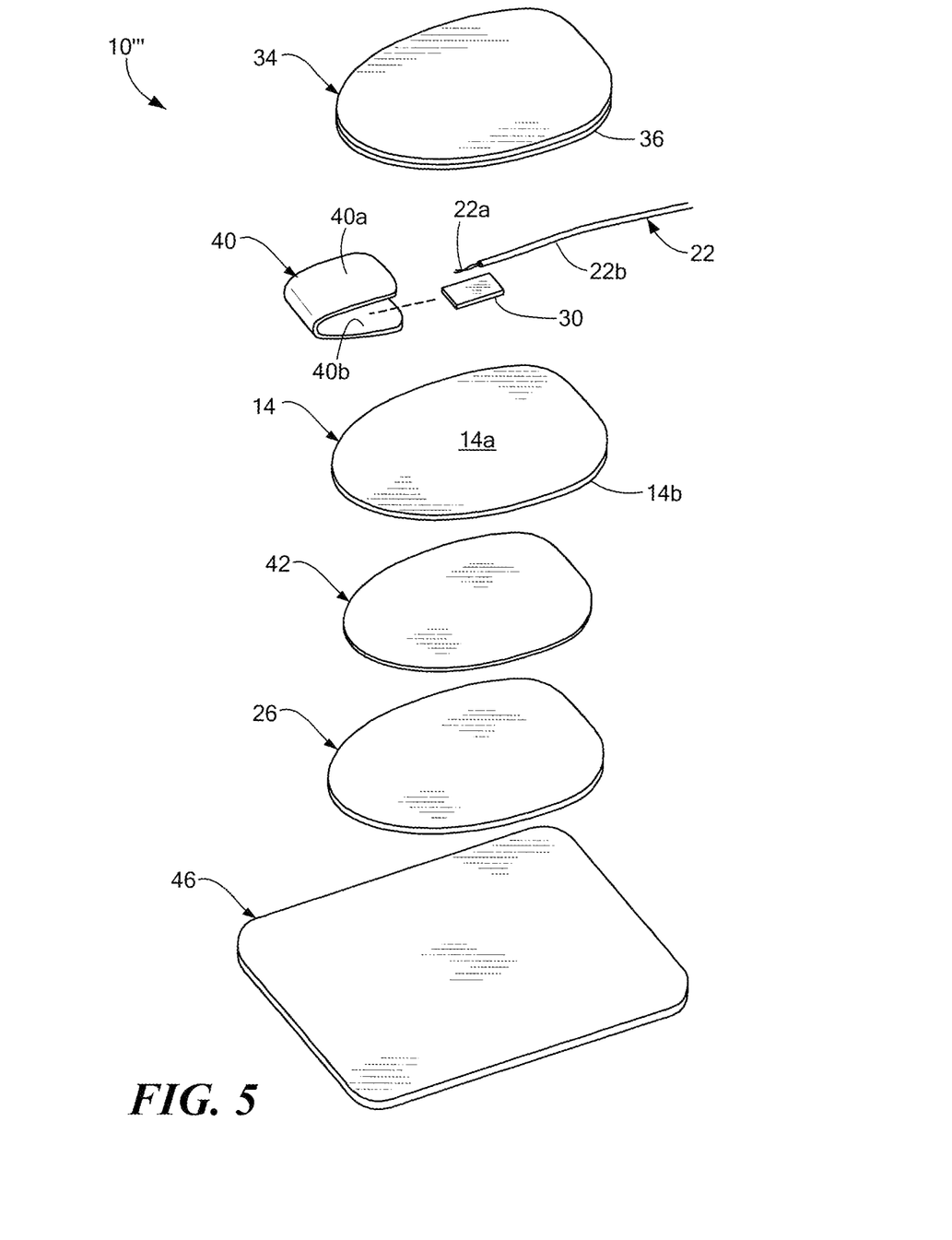
FIG. 5 is a perspective exploded view of a medical electrode according to yet another alternative embodiment.

A current distributing structure for conducting and distributing energy to the electrode member 14 may take various forms and positions in the electrode. In the embodiment of FIG. 1, the current distributing structure includes a current distributing layer 38 disposed between the unfanned, unsheathed conductor end portion 22a and an adhesive layer 36 of a cover sheet 34 and a current distributing mat 18 disposed between the energy blocking layer 30 and the top face 14a of the electrode member 14. The embodiments of FIGS. 3-5 show alternative arrangements for the current distributing structure.

In use, charge from the conductor end portion 22a is dispersed outward on the current distributing layer 38. The charge is transferred from the current distributing layer 38 to areas of the current distributing mat 18 in direct contact with the current distributing layer and is then transferred from the current distributing mat 18 to areas of the sheet electrode member 14 in direct contact with the current distributing mat. In this way, the current distributing layer 38 serves the function conventionally served by fanning out the individual conductor strands; namely, to disperse the electrical charge so as to effectively increase the contact area between the conductor 22 and the conductive mat 18.

The current distributing layer 38 may comprise a solid metallic foil, such as may comprise one or more of aluminum, tin, copper, brass, antimony, silver, gold, nickel, platinum, chromium, cadmium, pladmium, zinc, and indium. In one embodiment, the current distributing layer 38 is on the order 2 inches by 2 inches and comprises aluminum foil having a thickness on the order of 1 mil.

The current distributing mat 18 is configured to have electrical conductivity in the plane of the mat and transverse to the plane of the mat and a higher current carrying capacity than the electrode member 14. The mat 18 distributes current over a central area of the electrode member 14 and has an outer perimeter spaced inwardly of the perimeter of the electrode member. The mat 18 is sized to distribute the current uniformly over the central portion of the electrode member 14 in order to inhibit arcing through the central portion of the electrode member, and is spaced inwardly from the perimeter of the electrode member in order to avoid conveying high current levels to the outer periphery of the electrode member. For example, with an electrode member 14 having an area of about 80 cm$^2$, a mat area of about 25 cm$^2$ is generally sufficient to distribute the energy of defibrillation pulses over a sufficiently large area to avoid arcing through the electrode member.

The current distributing mat 18 may comprise a non-woven open mesh metallized carbon fiber web having an electrically conductive carbon impregnated pressure sensitive adhesive composition on the upper and lower surfaces of the web. The web of the mat 18 may be less than five mils thick and comprised of semi-metallic fibers, such as carbon fibers which are metal plated or coated before or after being formed into a web with a metal coating that is 35% to 40% by weight of the metal plated carbon fiber web. The semi-metallic carbon fibers are X-ray transparent before plating or coating and the metal plating or coating of the fibers of the web is sufficiently thin, for example less than ten microns in thickness, so that the thin open-mesh web formed of the metal plated fibers remains X-ray transparent.

The electrically conductive pressure sensitive adhesive that is applied to opposite surfaces of the web 18 is loaded with sufficient carbon or graphite for good electrical conductivity, so that the composite web and adhesive provide a mat that is electrically conductive in the plane of the mat and transverse to the plane of the mat. An example of a conductive double-faced pressure sensitive tape with a conductive carrier which can be used for the mat is a thin pressure sensitive bonding tape available from Adhesives Research, Inc., Glen Rock, Pa. under the trademark ARCLAD® product No. 8001.

Alternatively, the current distributing mat 18 may comprise a solid metallic foil or fine screen mesh covered with a conductive polymer adhesive for attaching the mat to the electrode member 14. The foil is on the order of 0.001-0.002 inches thick and suitable metals include copper or tin. Other metals may be used, such as gold, silver, nickel, aluminum, platinum, chromium, cadmium, pladmium, zinc, antimony, and indium.

As a further alternative, the current distributing mat 18 may comprise a conductive adhesive. One suitable adhesive is a urethane base that is impregnated with conductive beads or particles of carbon or graphite and metals, such as silver or titanium carbide, for conductivity.

In one embodiment, the adhesive has a sheet resistance of less than 1 ohm/in$^2$/mil. One such suitable electrically conductive adhesive may be obtained from Electron Microscopy Sciences of Hatfield, Pa., identified as "silver conductive coating 18 DB70X," "silver conductive adhesive fluid 504," and "silver conductive adhesive paste 478SS". The adhesive is applied to a selected area on the upper surface of the sheet electrode 14 by screen printing, pad printing, ink jet printing, flexographic printing or the like, and then cured by the application of heat, ultraviolet light, or electron beam, as examples. The adhesive may be applied to a thickness of from approximately 1 mil to 2 mils, which cures down to a thickness of less than 1 mil.

The electrode member 14 may be formed of a thin, flexible sheet of an electrically conductive polymer, such as graphite filled polyvinyl chloride film having a thickness on the order of two to four mils. The film may contain carbon black, acetylene black or other forms of carbon. An example of carbon filled polymer suitable for providing the electrode member 14 is thin carbon filled PVC available from Burkhardt/Freeman, Holyoke, Mass., under the trademark CONDUCTON.

Suitable dimensions for the electrode member 14 are dictated by the electrode application. For example, in the case of defibrillation electrodes, the electrode member 14 is dimensioned to have a surface area sufficient to achieve a current density distribution over an area of the patient's heart established in standard ANSI/AAMI IEC60601-2-4.

The electrode 10 may contain a conductive coating 42 in contact with at least a portion of the bottom face 14b of the electrode member 14. The outer perimeter of the coating 42 may be spaced inwardly from the perimeter of the electrode member 14. One example of conductive coating 42 comprises a metal and a metal halide, such as Fluoride, Chloride, Bromide, Iodide, Astatinide, and the like. One specific example of conductive coating 42 comprises a metal and a metal chloride, such as a silver/silver chloride ink coating, as may be applied in a layer or layers to the bottom face 14b of the electrode member by silk screening or flexographic printing. In one embodiment, the coating 42 is less than ten microns in thickness, which is sufficient to provide good electrical conductivity without impairing the X-ray transparency of the electrode member. A carbon filled PVC material with silver/silver chloride coating on the underside suitable for use as the electrode member and coating is available from Prime Label And Screen, Inc., New Berlin, WI. Alternatively, the metal/metal chloride coating 42 can comprise a single layer, chloride-coated metallic foil coated with a conductive acrylic adhesive. The metallic foil may comprise silver, tin, copper, nickel, gold, aluminum, platinum, chromium, cadmium, pladmium, zinc, antimony, or indium covered with an adhesive such as the ARCLAD® 8001 bonding tape or ARCLAD® EC2 adhesive.

The conductive coating 42 may have a variation or gradient in impedance from center to edge in order to reduce the current density at the electrode edges which can result in skin irritation or burning. As one example, disclosed in U.S. Pat. No. 6,600,957, the silver/silver chloride ink coverage or concentration is 100% in a central area of the coating 42 and the percentage of coverage or concentration decreases linearly, reaching zero at the outer edge of the coating. Alternatively, or in addition, the variation in impedance may comprise step changes in impedance.

An impedance gradient may also be achieved by forming the conductive coating 42 with two-layers as described in U.S. Pat. No. 7,742,828. More particularly, the coating 42 may be formed in two layers each of a few microns in thickness with a first layer having an outer perimeter spaced inwardly of the perimeter of the electrode member 14 and a second layer having an outer perimeter spaced inwardly from the perimeter of the first layer. The second layer may be applied first with the first layer underlying the second layer. The dual layers provide higher electrical conductivity in the area where the layers overlap, with the conductivity stepping down in the single layer and decreasing to the conductivity of the carbon filled polymer of the electrode member 14 in the area outward of the coating. The area where the layers overlap, which corresponds to the area of the first layer, may be made substantially equal to the minimum active electrode area prescribed by ANSI/AAMI IEC60601-2-4.

Alternative ways to achieve a desired impedance gradient from center to edge of the coating 42 are shown in connection with FIGS. 3 and 4 below. It will be appreciated that the various approaches to achieve an impedance variation can be combined.

The patient contacting layer 26 is in electrical contact with the electrode member 14 and may comprise one or more of an electrically conductive gel layer, a gel pad containing electrically conductive gel, and an electrically conductive adhesive. In one embodiment, the patient contacting layer 26 comprises a pad of electrically conductive gel in contact with a release cover sheet 46 prior to the use of the electrode. The gel pad may be approximately 65 mm wide and 122 mm long. The gel pad 26 may comprise a skin compatible conductive hydrogel or adhesive having good ability to retain moisture content and sufficient adhesive to adhesively secure the electrode to the patient's skin. Examples of suitable hydrogels include conductive hydrogels commercially available from the Kendall-LTP division of Tyco Healthcare Group LP, Mansfield, Mass., such as RG-73P4 conductive hydrogel.

A removable release carrier sheet 46 covers and protects the patient contacting layer 26 and is adapted to be removed for use of the electrode on a patient. Release carrier sheet 46 may comprise, for example, of silicone-coated polyethylene terephthalate (PET). Although not required, a rectangular shape is suitable for the release carrier sheet 46. If rectangular as illustrated, dimensions such as a length of about 140 mm and a width of about 82 mm are suitable.

The cover sheet 34 may be a continuous foam backing sheet without any openings and having a thickness of about 1 mm. In the illustrative embodiment, the cover sheet 34 and the patient contacting layer 26 are coextensive and coterminous so that once the release carrier sheet 46 is removed, the cover sheet 34 and patient contacting layer 26 form a single peripheral edge for the electrode. Alternatively, the cover sheet dimensions may be larger than the patient contacting layer 26 so that the adhesive layer 36 on the cover sheet adheres to the patient's skin in use.

The adhesive layer 36 secures the cover sheet 34 to the current distributing layer 38 and the top face 14a of the electrode member 14. The adhesive layer 36 may be a pressure sensitive adhesive, such as thermoplastic hot melt adhesive. In one embodiment, the adhesive layer 36 is non-conductive. One example of a pressure sensitive adhesive is V-88 available from FLEXcon, Spencer, Mass.

The electrical conductor 22 includes one or more conductive strands comprising one or more of metal wires and conductive metal-coated fibers. The conductor 22 has an electrically insulative sheath 22b and an unfanned, unsheathed end portion 22a that is conductively coupled to the electrode member 14. In one embodiment, the unsheathed end portion has a length on the order of 1.25 inches. By "unfanned" it is meant generally that the individual conductors are not fanned or spread out or otherwise separated, whether by manual or automated means. As such, once the conductor sheath 22b is removed to expose the unsheathed end portion 22a, it can be expected that some, and probably most, of the conductor strands will contact or overlap each other in some fashion. As a few examples, the strands may be twisted or braided or may simply be substantially parallel, but in contact or close to each other, with no intentional separating performed during manufacture.

The unsheathed end portion 22a is not fanned thereby enhancing the ease of manufacturing (as compared to conventional manual fanning of individual conductor strands) and reducing the associated manufacturing cost. Energy from the unfanned conductor end portion 22a is blocked by the energy blocking layer 30 and thereby caused to be transferred to the current distributing layer 38 where it disperses for transfer to the electrode member 14. In this way, the current distributing layer 38 serves to increase the effective contact area between the conductor end portion 22a and the electrode member 14 and thus, serves the purpose conventionally served by fanning the conductor strands.

In some applications it is desirable that conductor 22, like the other components of the electrode, be X-ray transmissive. X-ray transmissive conductors may be formed of metallized carbon fiber tows with an insulating sheath formed of an X-ray transparent material. The carbon fiber tows may be of a size having between 3,000 to 12,000 fibers and metal plated with a metal coating that is about 20% to 50% by weight of the metal plated carbon fiber tow. The higher weight plating on the larger size tows provides improved current carrying capacity for repeated defibrillation pulses. Fiber tows may be made from a polyacrylonitrile precursor and are referred to as pan base carbon fiber and are commercially available from Amoco Performance Products, Inc., Atlanta, Ga. Since the density of the carbon fiber tows is very low as compared to the density of the metal coating, a metal coating of 30% to 40% by weight of the metal plated carbon fiber tow is very thin and is X-ray transparent. The metal coating may be nickel which provides good electrical conductivity and corrosion resistance at moderate cost, but other metals such as copper or silver or gold could be used alone or in combination with the nickel coating. In electrode applications where X-ray translucency is not required, the conductor 22 can be formed of metal such as copper, tin, silver, or gold.

In order to minimize the likelihood of pulling the conductor 22 relative to the electrode, the insulative sheath 22b may be heat softened and flattened against the unsheathed conductor end portion 22a by heated jaws, as shown in the above-referenced U.S. Pat. No. 5,824,033.

Various automated or semi-automated manufacturing processes are suitable for the electrode 10. In general, a method of fabricating the electrode 10 includes the steps of providing the electrode member 14, conductively coupling the unfanned, unsheathed end portion 22a of the electrical conductor 22 to the electrode member 14, and securing a patient contacting layer 26 to at least a portion of the bottom face 14b of the electrode member. The energy blocking layer 30 is positioned between the unfanned conductor end portion 22a and the electrode member 14. The method may further include securing a cover sheet 34 to the top face 14a of the electrode member 14 and a current distributing structure may be conductively secured to at least a portion of the top face 14a of the electrode member. Pressure is applied as necessary during manufacture to ensure contact between at least the unsheathed conductor end portion 22a and the current distributing layer 38.

Figure 2:
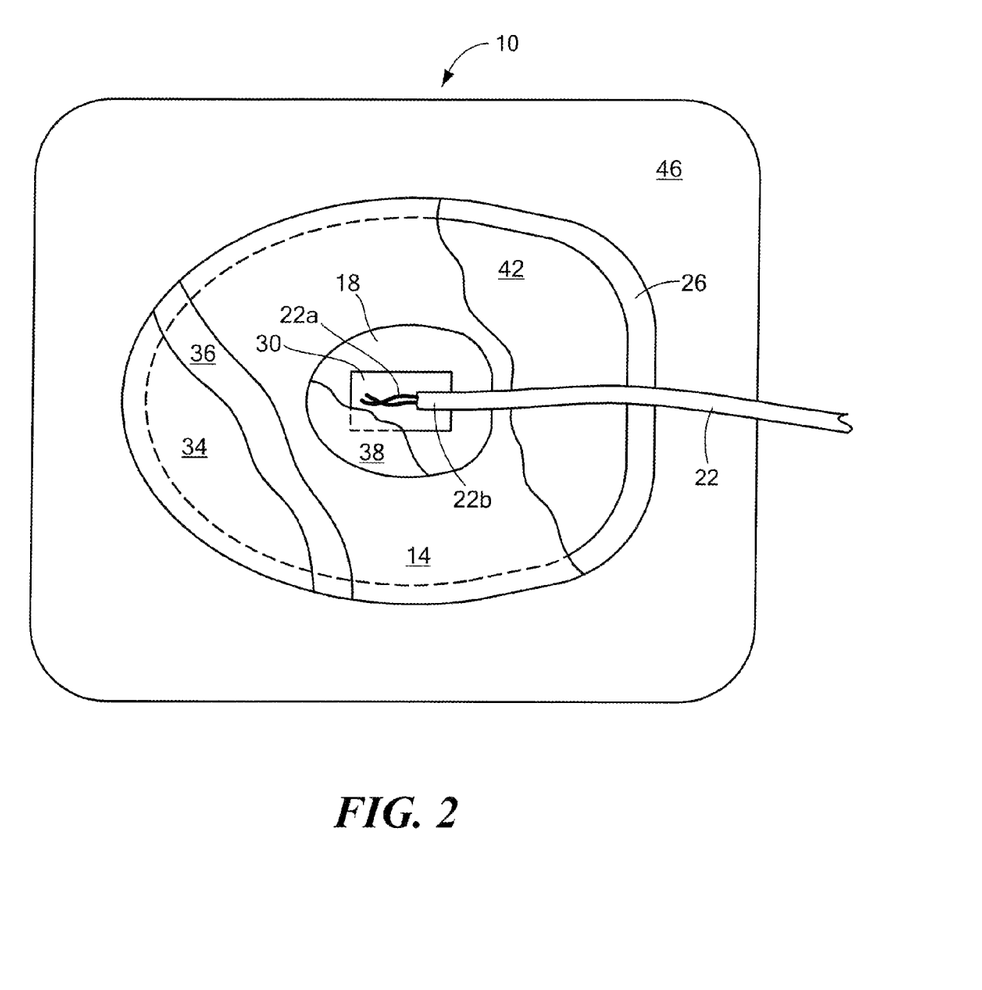
FIG. 2 is a top plan view of the medical electrode of FIG. 1.

Referring also to the top plan view of the electrode 10 in FIG. 2, illustrative relative dimensions and component placements are readily apparent. In the illustrative embodiment, the cover sheet 34, the electrode member 14, and the patient contacting layer 26 are coextensive and coterminous and form a single peripheral edge for the electrode once the release carrier sheet 46 is removed for use. The coating 42 may be spaced inwardly from the perimeter of the electrode member 14, as shown. The current distributing mat 18 and the current distributing layer 38 are coextensive and coterminous with a common outer perimeter spaced inwardly from the perimeter of the electrode member 14, as shown.

The energy blocking layer 30 is sized, and the untanned conductor end portion 22a is positioned relative to the energy blocking layer 30, so that the conductor end portion is entirely contained within the perimeter of energy blocking layer, as is desirable to prevent immediate charge transfer from the conductor to the electrode member. However, it is desirable for the blocking layer 30 to be as small as possible while still containing the unsheathed conductor end portion 22a in order to thereby permit the current distributing layer 38 to directly contact as much area of the current distributing mat 18 as possible for effective distribution and transfer of current.

While illustrative dimensions and shapes for the electrode components are shown herein, it will be appreciated by those of ordinary skill in the art that such characteristics are examples only and in many cases, can be readily varied to suit particular application, cost, and manufacturability requirements. Furthermore, while X-ray transmissivity can be achieved in each of the above-described components of the electrode 10, it will be appreciated that all or some portion of the electrode components may be designed to achieve this characteristic as desired to suit the requirements of a particular electrode application.

Referring also to FIG. 3, in which like elements are labeled with like reference characters, an alternative electrode embodiment 10' is shown. The electrode 10' differs from the embodiment of FIG. 1 in that here, the current distributing structure includes only the current distributing layer 38 (i.e., the mat 18 is omitted as may be desirable to reduce costs). Thus, in electrode 10', current is transferred from the conductor end portion 22a to the layer 38 where it is distributed outward and transferred directly to the electrode member 14, a central portion of which (surrounding the energy blocking layer 30) is in contact with the layer 38.

The electrode 10' also differs from the electrode 10 (FIG. 1) in that the conductive coating 42' has undulating edges, as may be scalloped or serrated edges. Such edges serve to decrease the current density at the periphery of the electrode member 14, thereby minimizing the likelihood of skin irritation and burns. It will be appreciated that this technique for achieving an impedance gradient from the center to the edges of the coating 42' may be used alone or in combination with other techniques described herein.

Referring also to FIG. 4, in which like elements are labeled with like reference characters, a further alternative electrode embodiment 10" has a current distributing structure in the form of the current distributing layer 38 and the current distributing mat 18. However here, the current distributing mat 18 is positioned between the unsheathed conductor end portion 22a and the energy blocking layer 30 (rather than being positioned between the energy blocking layer and the electrode member 14 as in FIG. 1). Thus, in electrode 10", current is transferred from the conductor end portion 22a to both layer 38 and to mat 18 simultaneously where it is distributed outward and transferred to portions of the electrode member 14 through areas of the conductive mat that are in contact with the electrode member (i.e., areas of the conductive mat other than the area in contact with the energy blocking layer 30).

The electrode 10" also differs from the electrode 10 (FIG. 1) in that the conductive coating 42" has a variable thickness such that the coating is thickest at its center and thins at its edges so as to decrease the current density at the perimeter of the electrode member 14 as is desirable to minimize skin irritation and burns. Here again, this technique for achieving an impedance gradient from the center to the edges of the coating may be used alone or in combination with other techniques described herein.

Referring also to the further electrode embodiment 10''' of FIG. 5, in which like elements are labeled with like reference characters, the electrode 10''' differs from the embodiment of FIG. 1 in that here, the current distributing structure takes the form of a folded structure 40 having a first portion 40a positioned between the unfanned conductor end portion 22a and the cover sheet 34 (taking the place of layer 38 in FIG. 1) and a second portion 40b positioned between the energy blocking layer 30 and the electrode member 14 (taking the place of mat 18 in FIG. 1). Alternatively, the folded structure 40 can replace elements 18 and 38 of FIG. 4 in which case only the unsheathed conductor end portion 22a is sandwiched between the folded portions 40a and 40b and the energy blocking layer 30 is disposed between the folded portion 40b and the electrode member 14. The folded structure 40 may comprise a current distributing layer or mat and further may comprise one or more of a mat comprising a metalized carbon fiber web, a solid metallic foil, and an electrically conductive adhesive Referring also to FIG. 6, a medical device 50, as may take the form of an ECG monitor, a defibrillator, a transcutaneous stimulation device, an electrosurgical device, or a combination device as just a few examples, is connected through conductors 54a, 54b to a polarized connector 58. Electrodes 10a, 10b are positioned on the patient and may take the form of any of the above-described electrode embodiments.

Figure 6:
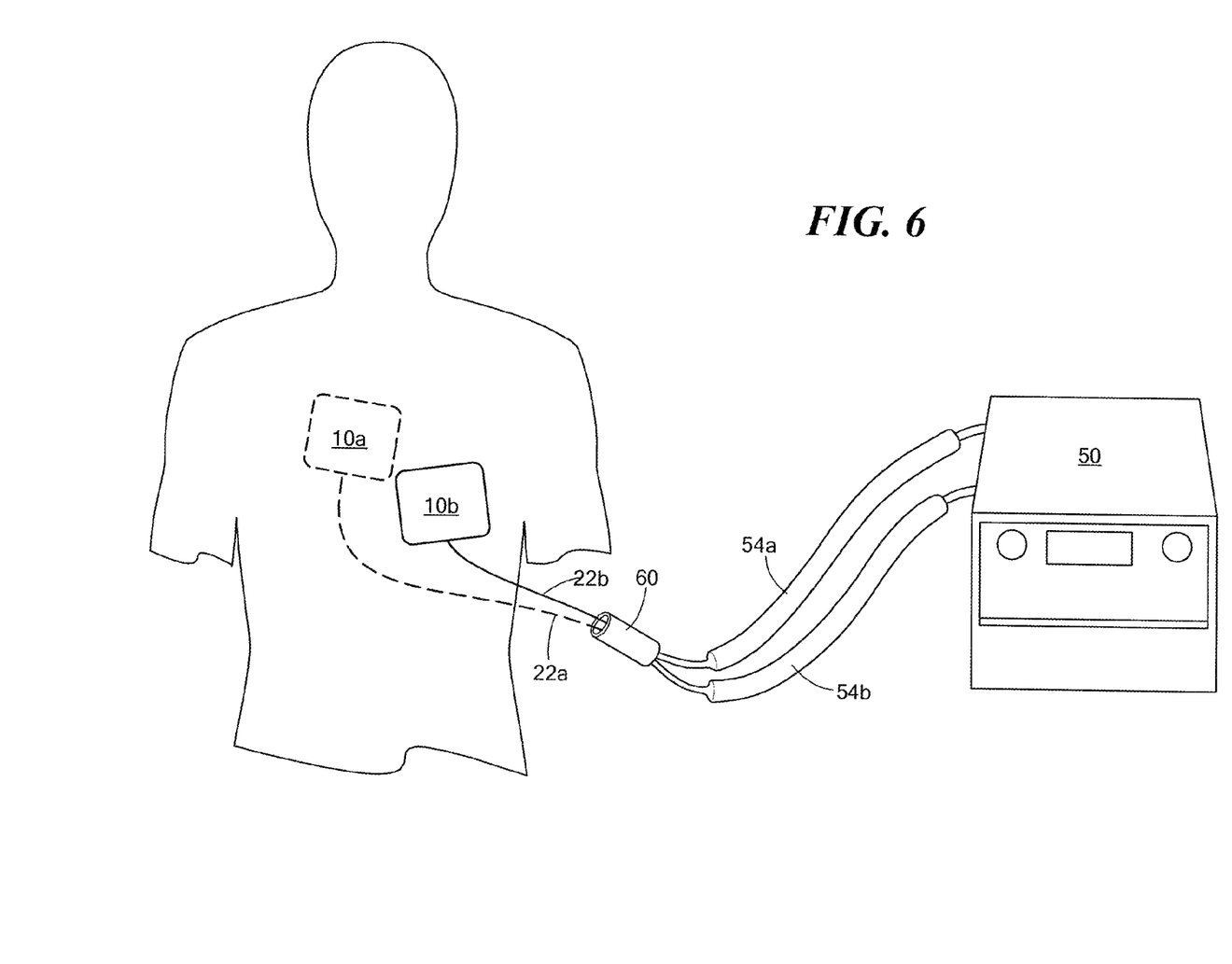
FIG. 6 is a diagrammatic view of application of the electrodes to a patient and connection of the electrodes to a medical device.

Conductors 22a, 22b of respective electrodes 10a, 10b terminate at a connector 60 that is adapted for coupling to the device connector 58, as shown. Since the electrodes 10a, 10b are X-ray transparent, they can be positioned on the patient at any customary position used for defibrillation for example without adversely affecting X-rays of the patient's chest in areas underlying the electrodes.

Having described preferred embodiments, which serve to illustrate various concepts, structures and techniques, which are the subject of this patent, it will now become apparent to those of ordinary skill in the art that other embodiments incorporating these concepts, structures and techniques may be used. Accordingly, it is submitted that that scope of the patent should not be limited to the described embodiments but rather should be limited only by the spirit and scope of the following claims.

What is claimed is:

1. A medical electrode comprising:
an electrode member having a top face and a bottom face;
an electrical conductor having an unfanned, unsheathed end portion for conducting energy between the electrode member and a medical device;
an energy blocking layer disposed between the electrode member and the unfanned, unsheathed end portion of the electrical conductor; and
a patient contacting layer secured to at least a portion of the bottom face of the electrode member.

2. The medical electrode of claim 1 wherein the energy blocking layer comprises a hydrophobic polymeric film.

3. The medical electrode of claim 1 further comprising a current distributing structure for conducting and distributing energy to an area of the electrode member.

4. The medical electrode of claim 3 further comprising a cover sheet secured to at least a portion of the top face of the electrode member.

5. The medical electrode of claim 4 wherein the current distributing structure is disposed between the unfanned, unsheathed end portion of the electrical conductor and the cover sheet.

6. The medical electrode of claim 5 wherein the current distributing structure comprises a solid metallic foil.

7. The medical electrode of claim 6 wherein the solid metallic foil comprises one or more of aluminum, tin, copper, brass, antimony, silver, gold, nickel, platinum, chromium, cadmium, pladmium, zinc, and indium.

8. The medical electrode of claim 5 wherein a first portion of the current distributing structure is disposed between the unfanned, unsheathed end portion of the electrical conductor and the cover sheet and a second portion of the current distributing structure is disposed between the energy blocking layer and the top face of the electrode member.

9. The medical electrode of claim 8 wherein the first and second portions of the current distributing structure comprise at least one of a mat comprising a metalized carbon fiber web, a solid metallic foil, and an electrically conductive adhesive.

10. The medical electrode of claim 5 wherein a first portion of the current distributing structure is disposed between the unfanned, unsheathed end portion of the electrical conductor and the cover sheet and a second portion of the current distributing structure is disposed between the unfanned, unsheathed end portion of the electrical conductor and the energy blocking layer.

11. The medical electrode of claim 10 wherein the first and second portions of the current distributing structure comprise at least one of a mat comprising a metalized carbon fiber web, a solid metallic foil, and an electrically conductive adhesive.

12. The medical electrode of claim 1 wherein the patient contacting layer comprises one or more of an electrically conductive gel layer, a gel pad containing electrically conductive gel, and an electrically conductive adhesive.

13. The medical electrode of claim 1 further comprising a conductive coating in contact with at least a portion of the bottom face of the electrode member.

14. The medical electrode of claim 13 wherein the conductive coating comprises a metal and a metal chloride.

15. The medical electrode of claim 14 wherein the metal is silver and the metal chloride is silver chloride.

16. The medical electrode of claim 1 wherein the electrode member comprises an electrically conductive polymer.

17. The medical electrode of claim 16 wherein the electrically conductive polymer comprises polyvinyl chloride and one or more forms of carbon black.

18. The medical electrode of claim 1 wherein the electrical conductor comprises one or more of metal wires and conductive metal-coated fibers.

19. The medical electrode of claim 1 further comprising a removable release carrier sheet covering the patient contacting layer and adapted to be removed from the electrode for use of the electrode on a patient.

20. The medical electrode of claim 1 wherein the electrode is transmissive to X-rays.

21. A method for fabricating a medical electrode comprising the steps of:
- providing an electrode member with a top face and a bottom face;
- conductively coupling an unfanned, unsheathed end portion of an electrical conductor to the top face of the electrode member, the electrical conductor adapted to conduct energy between electrode member and a medical device;
- providing an energy blocking layer between the unfanned, unsheathed end portion of the electrical conductor and the top face of the electrode member; and
- securing a patient contacting layer to at least a portion of the bottom face of the electrode member.

22. The method of claim 21 wherein the step of conductively coupling an unfanned, unsheathed end portion of the electrical conductor to the electrode member further comprises the step of securing a current distributing structure to at least a portion of the top face of the electrode member.

23. The method of claim 22 wherein the step of securing a current distributing structure to at least a portion of the top face of the electrode member comprises the step of disposing a first portion of the current distributing structure between the unfanned, unsheathed end portion of the electrical conductor and a cover sheet and disposing a second portion of the current distributing structure between the energy blocking layer and the top face of the electrode member.

\* \* \* \* \*